(12) United States Patent
Babko-Malyi et al.

(10) Patent No.: US 11,484,692 B2
(45) Date of Patent: Nov. 1, 2022

(54) BALLOON CATHETER AND FLUID MANAGEMENT SYSTEM THEREOF

(71) Applicant: CardioFocus, Inc., Marlborough, MA (US)

(72) Inventors: Sergei Babko-Malyi, Marlborough, MA (US); Brian Estabrook, Foxboro, MA (US); Gerald Melsky, Lexington, MA (US); Richard Thompson, Marlborough, MA (US)

(73) Assignee: CARDIOFOCUS, INC., Marlborough, MA (US)

( * ) Notice: Subject to any disclaimer, the term of this patent is extended or adjusted under 35 U.S.C. 154(b) by 105 days.

(21) Appl. No.: 17/024,269

(22) Filed: Sep. 17, 2020

(65) Prior Publication Data

US 2021/0069479 A1 Mar. 11, 2021

Related U.S. Application Data

(63) Continuation of application No. 15/953,628, filed on Apr. 16, 2018, now Pat. No. 10,806,910.

(60) Provisional application No. 62/485,700, filed on Apr. 14, 2017.

(51) Int. Cl.
*A61M 25/10* (2013.01)

(52) U.S. Cl.
CPC ............. *A61M 25/10181* (2013.11); *A61M 25/10184* (2013.11); *A61M 25/10186* (2013.11); *A61M 2025/1022* (2013.01); *A61M 2025/1072* (2013.01); *A61M 2205/3331* (2013.01); *A61M 2205/3606* (2013.01); *A61M 2205/502* (2013.01); *A61M 2205/7536* (2013.01)

(58) Field of Classification Search
CPC ............ A61M 25/10; A61M 25/10185; A61M 25/10186; A61M 25/10181; A61M 25/10184; A61M 2025/1022; A61M 2025/1072; A61M 2025/3331; A61M 2025/3606; A61M 2025/7536; A61M 2025/502

See application file for complete search history.

(56) References Cited

U.S. PATENT DOCUMENTS

| | | |
|---|---|---|
| 2003/0229264 A1 | 12/2003 | Connors et al. |
| 2004/0111138 A1 | 6/2004 | Bleam et al. |
| 2005/0209662 A1 | 9/2005 | Lunderqvist et al. |
| 2011/0202084 A1 | 8/2011 | Hoem et al. |
| 2013/0079737 A1 | 3/2013 | Hanuka et al. |
| 2014/0121515 A1 | 5/2014 | Vitullo et al. |

*Primary Examiner* — Paula J Stice
(74) *Attorney, Agent, or Firm* — Leason Ellis LLP

(57) ABSTRACT

A method for maintaining a balloon of a balloon catheter at a prescribed pressure of between about 0.2 psi and 1 psi comprises the step of: generating a vacuum within a reservoir defined in a burette that is part of a fluid management system that is configured to controllably inflating and deflating the balloon by circulating balloon fill media along a fluid circuit, wherein generating the vacuum results in formation of a pressure differential along the fluid circuit, thereby allowing the balloon to be maintained at the prescribed pressure between about 0.2 psi and about 1 psi.

10 Claims, 3 Drawing Sheets

BALLOON CATHETER AND FLUID MANAGEMENT SYSTEM THEREOF

CROSS REFERENCE TO RELATED APPLICATIONS

Figure 1:
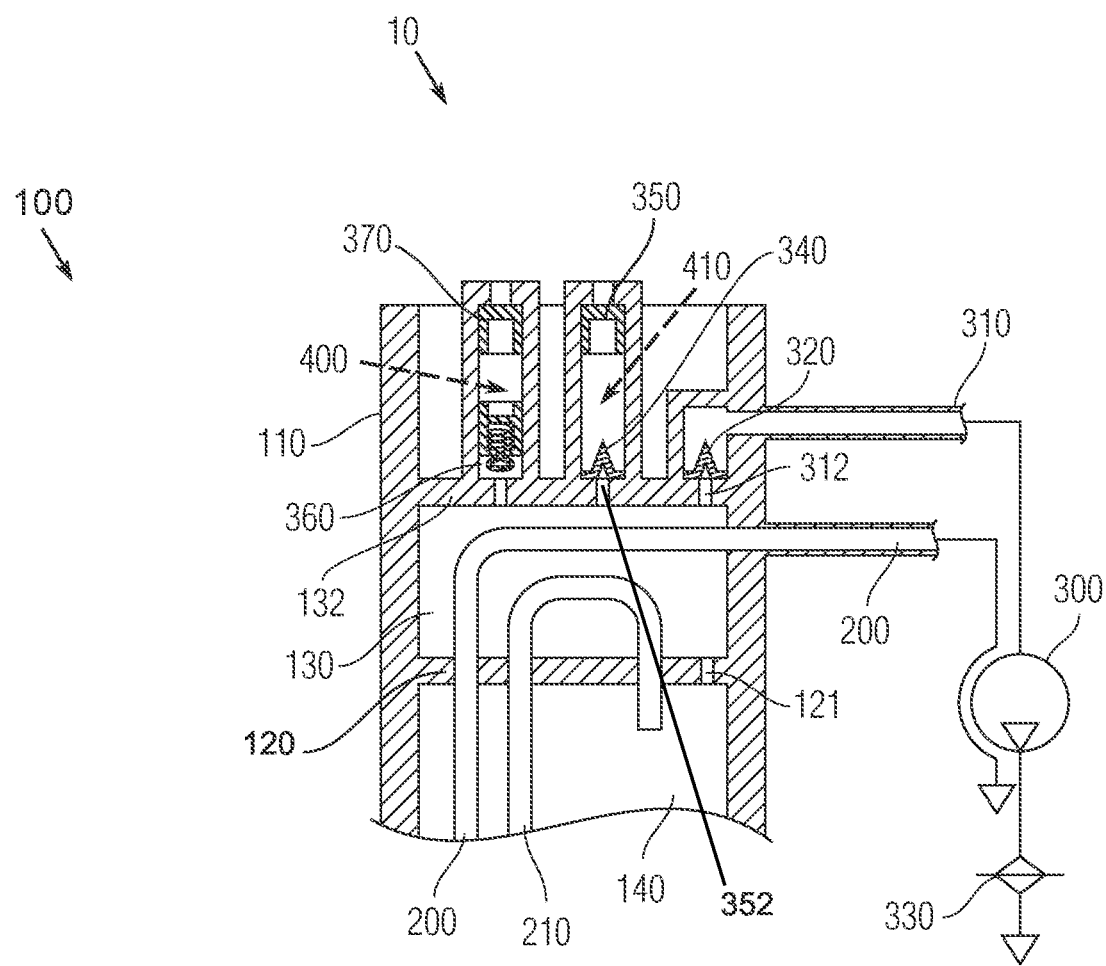

The present application is a continuation of patent application Ser. No. 15/953,628, filed Apr. 16, 2018, now U.S. Pat. No. 10,806,910, issued Oct. 20, 2020, which claims priority to U.S. patent application Ser. No. 62/485,700, filed Apr. 14, 2017 and is related to U.S. patent application Ser. No. 62/443,270, filed Jan. 6, 2017 and U.S. patent application Ser. No. 62/485,691 filed on Apr. 14, 2017, and U.S. patent application Ser. No. 15/863,373, filed on Jan. 5, 2018, and International Patent Application serial No. PCT/US2018/012715, filed Jan. 6, 2018, which are hereby expressly incorporated by reference in their respective entireties.

FIELD OF INVENTION

The present invention relates to balloon catheters used to treat atrial fibrillation and other medical conditions. In particular, the present invention relates to systems and methods for controlling fill media in the balloon catheter.

BACKGROUND

Balloon catheters can be used for a variety of medical procedures, including in the treatment of atrial fibrillation. In certain types of balloon catheters, a fill media is used to inflate the balloon and maintain the balloon at the inflated state while the procedure is performed. Once the balloon has been inflated to the desired size and pressure, the balloon fill media is circulated into and out of the balloon to keep the balloon temperature cool such that it does not damage the tissue of the patient. Conventionally, balloon catheters have been filled to pressures of 2 to 5 PSI. However, some balloon catheters now have lower pressures which allow for the balloon catheter to achieve greater contact with the patient's tissue. The prior art methods for cooling the balloon, however, are not compatible with balloons having a lower PSI. In particular, achieving the desired lower PSI using the prior art systems would require a lower flow rate of the fill media; however, this lower flow rate of the fill media is not adequate to keep the balloon and catheter components cool.

Additionally, in conventional designs, the operator/manipulator (e.g., physician) of the balloon catheter in the body of the patient relies on a separate, remote operator to inflate (or deflate) the balloon catheter to the desired size and pressure. As such, at least two operators are required in order to perform a medical procedure using the balloon catheter, as the operator who manipulates the balloon in the body of the patient must rely on a separator operator to inflate or deflate the balloon catheter.

Accordingly, the present systems and methods address these and other problems associated with balloon catheters.

SUMMARY

The present application relates to systems and methods for controlling fill media in the balloon catheter.

In a first aspect, a balloon catheter system is disclosed. The system comprises a balloon catheter, which includes a catheter body and an inflatable balloon coupled to one end of the body. The system further comprises a fluid management system for controllably inflating and deflating the balloon. The fluid management system includes a reservoir for storing balloon fill media, and a first conduit connected between the reservoir and the balloon for delivering the balloon fill media. The fluid management system further includes a second conduit connected between the balloon and the reservoir for returning the balloon fill media from the balloon to the reservoir, and a pump disposed along the first conduit. The pump is configured to circulate the balloon fill media along a circuit defined by the first and second conduits.

In one embodiment, a balloon catheter system includes a balloon catheter that includes a catheter body and an inflatable balloon coupled to one end thereof and a fluid management system for controllably inflating and deflating the balloon. The fluid management system includes a reservoir for storing balloon fill media, a first conduit connected between the reservoir and the balloon for delivering the balloon fill media, and a second conduit connected between the balloon and the reservoir for returning the balloon fill media from the balloon to the reservoir. A pump is disposed along the first conduit and configured to circulate the balloon fill media along a circuit defined by the first and second conduits. A vacuum conduit is in fluid communication with the reservoir and is acted upon by the pump to create negative pressure within the vacuum conduit which in turn results in a pressure drop within the reservoir and creation of a pressure differential along the circuit, thereby allowing the balloon to have a pressure between about 0.2 psi and about 1 psi.

These and other aspects, features, and advantages can be appreciated from the accompanying description of certain embodiments of the invention and the accompanying drawing figures and claims.

BRIEF DESCRIPTION OF THE DRAWING FIGURES

Figure 2:
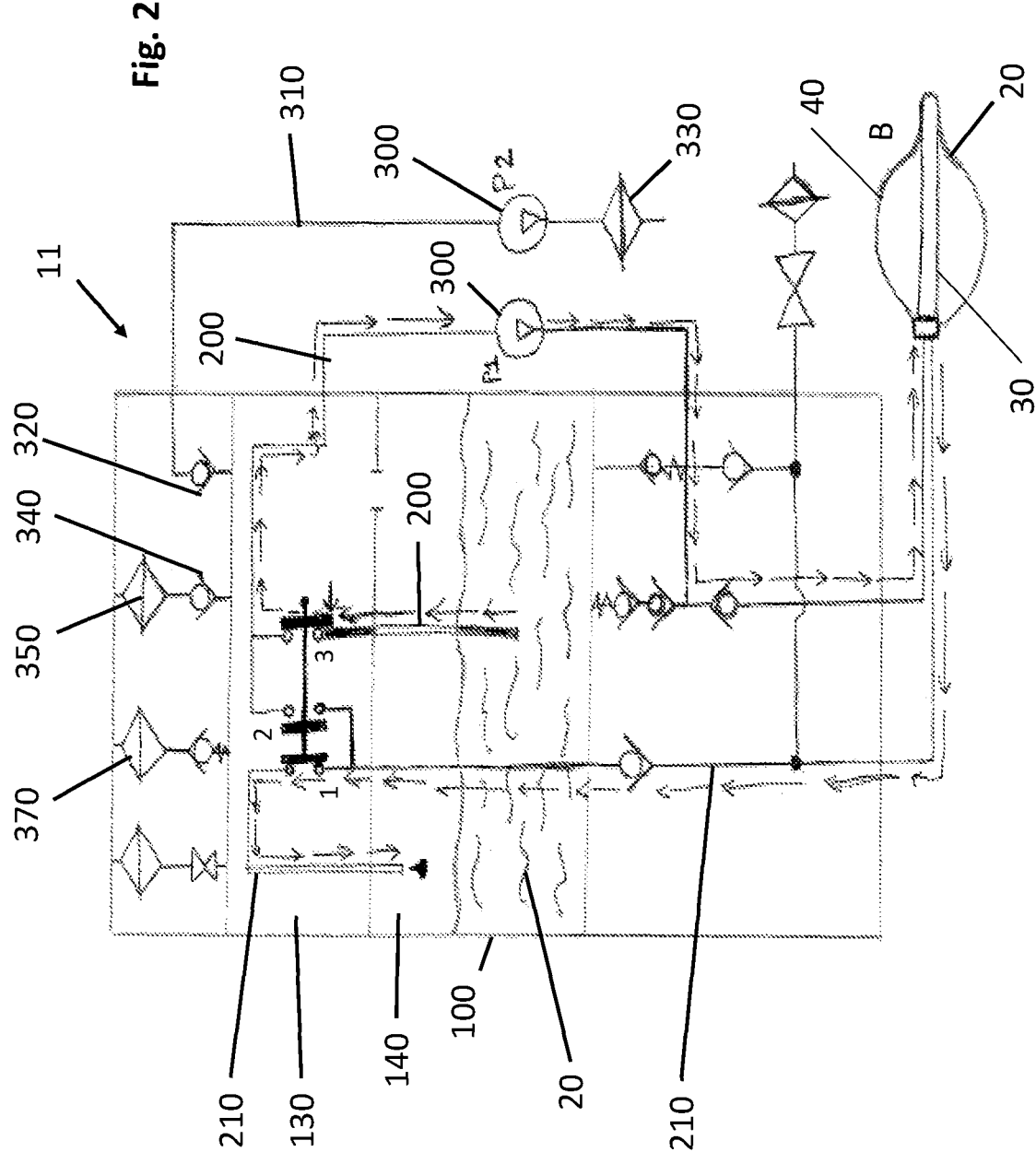
Figure 3:
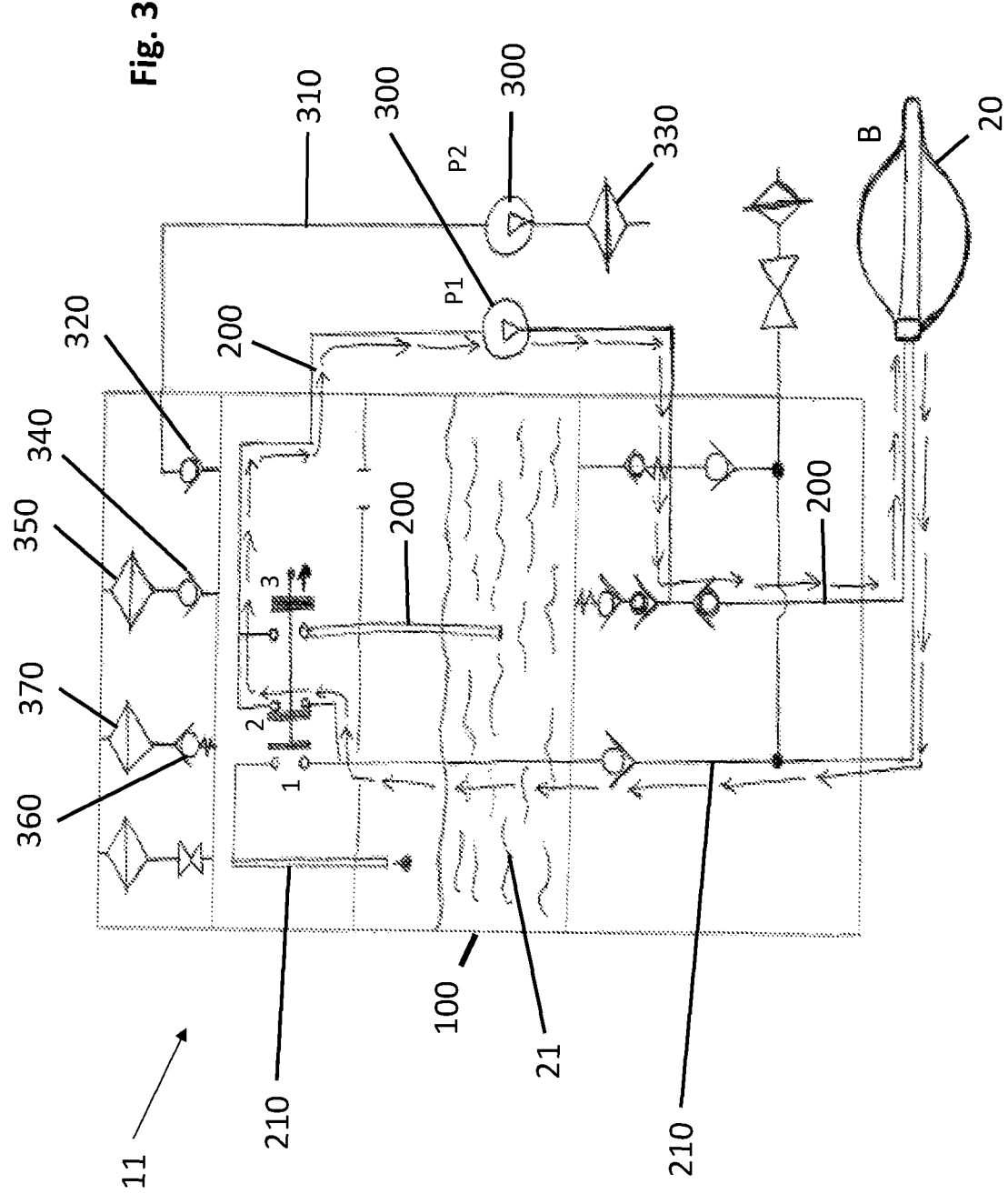

FIG. 1 displays a schematic of a balloon cooling system featuring a peristaltic pump in accordance with one or more embodiments;

FIG. 2 shows a flow diagram of the catheter of the balloon cooling system with the burette operating in normal mode in accordance with one or more embodiments; and FIG. 3 shows a flow diagram of the catheter of the balloon cooling system with the burette operating in trapped volume mode in accordance with one or more embodiments.

DETAILED DESCRIPTION OF CERTAIN EMBODIMENTS

The present disclosure details fluid control systems for filling a balloon catheter with fill media. The fluid control systems of the present disclosure are configured to inflate the balloon catheter to a desired pressure (e.g., approximately 0.2 to 1.0 PSI), maintain the balloon at the desired pressure for a desired duration during the medical procedure (e.g., ablation of heart tissue to treat atrial fibrillation), and deflate the balloon catheter to a desired pressure (or deflate the balloon catheter completely for removal of the catheter from the body). The present fluid control systems allow the balloon catheter to inflate and maintain the balloon catheter at a lower pressure, while keeping the balloon and catheter components cool such that the tissue of the patient is not damaged. Further, the present systems allow a single operator to control the inflation and deflation of the balloon catheter as well as the manipulation of the balloon catheter in the body of the patient during the medical procedure.

Balloon Cooling Systems

In one or more embodiments, the present application discloses a cooling system that is part of a balloon catheter system 10 that utilizes a single head peristaltic pump to circulate fluid as well as to create negative pressure in the burette (balloon fill media reservoir). As discussed herein, it is an objective of the present invention to provide a cooling system that can be used with a balloon catheter and is configured to permit the balloon catheter to be inflated to lower pressures, on the order of between about 0.2 psi to about 1 psi, which is substantially lower than traditional balloon inflation pressures. In order to achieve such inflation pressures, the cooling system is tailored to provide pressures along the cooling circuit that allow the balloon to achieve and maintain such lower balloon pressures.

In FIGS. 2 and 3, an alternative system 11 is shown and includes a balloon catheter that is generally indicated at 20 and includes a catheter body 30 and a balloon 40. As described herein, the balloon 40 of the balloon catheter 20 is fluidly connected to a source of fluid that not only cools the balloon but also serves as a means for inflating and deflating the balloon. As will be appreciated, a prescribed flow rate of cooling fluid is required in order to maintain the desired cooling of the balloon. However, control of the flow rate of the cooling fluid is required in order to avoid undesired inflation or deflation of the balloon. Thus, when the balloon is inflated to its desired inflation level, the cooling fluid is to be maintained at the desired flow rate to achieve cooling of the balloon and allow the balloon to maintain the lower inflation pressures described herein.

FIG. 1 shows an exemplary balloon catheter system 10 that includes the burette (reservoir) 100 with peristaltic vacuum assist option. The burette 100 holds the inflation fluid that is used to inflate the balloon of catheter (See, balloon catheter 20 of FIG. 2) and similarly, when deflation of the balloon is desired, this inflation fluid is withdrawn from the balloon at a faster rate than delivery of the inflation fluid to the balloon to cause deflation of the balloon. The burette 100 has a housing 110 that has a hollow interior (reservoir) for holding the inflation fluid indicated at 21 in FIGS. 2 and 3. The illustrated housing 110 has an inner partition wall 120 that partitions the reservoir into a first compartment (chamber) 130 and a second compartment (chamber) 140. The first compartment 130 is formed at one end of the housing 110 and the second compartment 140 is formed at the other end of the housing 110 and in particular, the first compartment 130 is at the top end, while the second compartment 140 is at the bottom end.

The first compartment 130 and second compartment 140 can have different sizes (volumes) and in particular, the second compartment 140 has a greater size than the first compartment since the second compartment 140 holds the inflation fluid, while the first compartment 130 is an air chamber.

As shown, the inner partition wall 120 has a through hole (vent hole) 121 that allows for fluid communication between the second compartment 140 and the first compartment 130.

The top of the first compartment 130 is defined by a top wall 132. As described herein, the top wall 132 includes a number of holes to define various flow paths.

For sake of simplicity, FIG. 1 only shows a portion of the housing 110 and does not show the balloon catheter 20 shown in FIG. 2; however, it will be understood that conduits 200, 210 in FIG. 1 lead to the balloon catheter 20 as shown in FIG. 2. A first conduit 200 that extends from the burette 100 to the balloon is shown and serves as an inflation line that delivery the inflation fluid to the balloon and thus is in fluid communication with the second compartment 140 so that inflation fluid can be drawn into the inflation line and delivered to the balloon. A second conduit 210 extends from the balloon to the burette 100 and serves as a return line that returns the inflation fluid from the balloon to the second compartment 140.

In accordance with the present invention, a pump 300 which can be in the form of a peristaltic pump is provided and acts upon the first conduit 200 to generate flow within the first conduit 200 and the second conduit 210 as well.

As mentioned, the present invention uses a vacuum assist feature to maintain the desired inflation pressures in the balloon. The vacuum assist feature includes a vacuum (third) conduit 310 that a first end that is in fluid communication with the first compartment 130 of the burette 100 and passes through a first through hole 312 that leads into the first compartment 130 to allow air within the first compartment 130 (and second compartment 140) to be evacuated. The vacuum conduit 310 is operatively coupled to a pump, such as a peristaltic pump, to generative negative pressure within the vacuum conduit 310. The pump can be a separate peristaltic pump or can be a single head peristaltic pump which acts both on the first conduit 200 and the vacuum conduit 310 to both pump the inflation fluid through the first conduit 200 and to generate the negative pressure within the vacuum conduit 310.

The burette 100 also includes an inlet 400 and an outlet 410 both of which are in fluid communication with the first compartment 130. More specifically, the inlet 400 comprises a fluid inlet for selectively allowing atmospheric air to flow into the first compartment 130 and the outlet 410 comprises a fluid outlet for selectively allowing fluid (gas or liquid or a mixture of both) to vent from the first compartment 130.

The vacuum system shown in FIG. 1 consists of peristaltic pump 300 (silicone tubing) connected to vacuum conduit 310 so that negative (relative to atmospheric) pressure is created in vacuum conduit 310 when pump 300 rotates in clockwise direction (direct). A first valve 320 which can be in the form of a first check-valve helps to prevent pressure build-up in the burette when pump rotates counterclockwise (reverse) and it also helps to prevent pulsations of pressure in the burette 100. The check valve 320 is thus located along the flow path of the vacuum conduit 310 and is adjacent the opening 312. The check valve 320 thus opens under negative pressure to open the interior of the burette 100 to the vacuum conduit 310.

An air filter 330 helps to prevent biocontaminants in the air from entering sterile environment of the burette 100.

Hole or opening 121 is needed for fluid communication between internal sections (first compartment 130 and second compartment 140) of the burette 100. A second valve 340 which can be in the form of a second check-valve that is selective fluid communication with the interior of the burette 100 (i.e., the first compartment 130 by means of a second opening 352 through wall 132). The second valve 340 is located along the outlet 410. Also within the outlet 410 is an air filter 350. The second valve 340 and air filter 350 are needed for the balloon deflation stage. During this stage (balloon deflation), liquid returns back into burette and compresses air in the head space (within second compartment 140). When this happens, the second valve 340 opens and allows air to exit the burette 100. Air Filter 350 prevents biocontaminants from entering the burette 100.

A third valve 360 is located along the inlet 400 and serves to allow atmospheric air to enter the burette 100 (through air filter 370 to avoid contamination of the burette 100) when pressure difference between the burette environment and the external atmosphere reaches the check pressure of the third valve 360. This helps to keep pressure in the burette 100 at constant level regardless of the rotational speed of the pump 300. This system helps to provide cooling of the balloon and maintaining the balloon pressure at gauge pressures down to zero, which allows one to use balloons made of very soft materials. The third valve 360 can be in the form of a spring-loaded valve that open and a prescribed applied force overcomes the opening force of the third valve 360. Thus, in the event, that the burette 100 is placed under excessive negative pressure due to operation of the peristaltic pump 300, the inlet 400 opens.

As discussed below, the vacuum assist of the present invention is required in order to achieve a pressure differential across the system to achieve the desired balloon pressures.

In order to maintain a prescribed flow rate along the fluid circuit, a prescribed pressure drop must be realized across the fluid circuit to ensure that the fluid flows from the burette 100 to the balloon and then returns back to the burette 100. However, in view of the very low pressures of the balloons in present system, pressure drop across the fluid circuit must accommodate such low balloon pressures. For example, if a pressure drop of 1 psi is required in order to maintain the desired flow rate of say 10 ml/minute, and the balloon is to be maintained at 0.2 psi, then the return line (conduit) 210 needs to operate under a pressure of −0.8 psi to produce the pressure drop of 1 psi across the system (cooling circuit). In order to achieve this pressure drop, the vacuum assist aspect of the invention is utilized and in particular, the burette 100 is maintained under vacuum as described herein. It will be appreciated that the preceding example is only exemplary in nature and other values are possible especially depending upon the targeted, selected flow rate of the cooling fluid that is required to maintain proper cooling of the balloon.

The present invention achieves this objective by providing the vacuum line 310 which generates negative pressure in the interior of the burette 100 to create the required pressure drop along the return line (line 210) to achieve the desired low pressure in the balloon.

FIG. 2 shows an alternative system 11 that is similar to the system 10 of FIG. 1. While two peristaltic pumps can be used, one operating on the vacuum conduit 310 and the other operating on the conduit 200, as mentioned with respect to FIG. 1, only a single pump 300 can be utilized to operate on both the vacuum conduit 310 and conduit 200.

More particularly, FIG. 2 shows a flow diagram of the balloon catheter 20 with the burette 100 operating in so called normal mode, where balloon pressure can be changed based on rotational speed of the peristaltic pump P1-P2 (same drive with two peristaltic tubes). In normal mode, valve 2 is closed and valves 1 and 3 are open that allows fluid in the balloon catheter 20 to communicate with fluid in the burette 100 (inflate/deflate). Additional valves can be added to allow a system to operate in constant volume mode. The liquid flow in the normal mode shown in FIG. 2 is indicated by the arrows.

FIG. 3 shows a flow diagram of the balloon catheter 20 with the burette 100 operating in so called trapped volume mode. The liquid flow is indicated by the arrows. In the trapped volume mode, valves 1 and 3 are closed and valve 2 is open causing the cooling liquid to have a constant volume which helps to keep the balloon 20 at the desired size by initially inflating it to this size and switching to the constant volume mode when the rotational speed of the pump 300 does not affect the balloon pressure. Again, it should be appreciated that in one or more embodiments, as exemplified in FIG. 3, one or more additional valves or pumps can be incorporated in the system.

In one or more embodiments, the balloon catheter 20 with the burette 100 can be operated in other modes, such as an inflate mode, a deflate mode, and a sterilization mode. In the inflate mode, valves 1 and 2 are closed, and valve 3 is open, allowing the fluid to be delivered from the burette and pumped into the balloon for inflation of the balloon. Conversely, in the deflate mode, valves 1 and 2 are open and valve 3 is closed, and as such the fluid is drawn out of the balloon and pumped back to the burette. Finally, in sterilization mode, valves 1, 2, and 3 are all partial open, thereby allowing fluid (in this case, sterilization fluid) to circulate throughout the system 11.

To assist the reader, the following Table sets forth the various operating modes of the present system as well as lists the operating state of the vacuum and the various valve positions are likewise indicated.

|  | Vacuum | Valve 320 | Valve 340 | Valve 360 | Valve 1 | Valve 2 | Valve 3 |
| --- | --- | --- | --- | --- | --- | --- | --- |
| Normal operating mode | On | Open | Closed | Conditionally opens | Open | Closed | Open |
| Trapped volume mode | On | Open | Closed | Conditionally opens | Closed | Open | Closed |
| Balloon inflation mode | On | Open | Closed | Conditionally opens | Closed | Closed | Open |
| Balloon deflation mode | On | Open | Open | Conditionally opens | Open | Open | Closed |
| Sterilization mode | On | Open | Closed | Conditionally opens | Partially open | Partially open | Partially open |

In one or more embodiments, valves 1-3 can be combined in a single block and operated with single lever that could switch between different operating modes. Valve design could use a number of different operating mechanisms. In a preferred configuration, the valve is based on pinched tubes, while in other configurations it can be trumpet valve or a stopcock type valve.

It will be appreciated that the vacuum assist feature permits the desired, target lower balloon pressures to be achieved in the balloon since if the burette was open to atmosphere, the balloon pressure cannot be lower than the pressure within the burette and thus, the low psi values cannot be achieved.

It will also be understood that any of the control systems described in the applications incorporated by reference herein can be used with the balloon catheters of the present invention. In particular, a console is typically provided with a graphical user interface that allows the user to enter certain information, such as balloon inflation level, and a processor of the controller can then calculate other operating parameters such as the required flow rate of the cooling fluid to achieve said inputted balloon inflation level. The controller then controls the valves described herein and the pump described herein to circulate the cooling fluid with the circuit and to inflate, deflate or maintain the balloon at the inputted inflation level.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:

1. A balloon catheter system, comprising:
    a balloon catheter including a catheter body and an inflatable balloon coupled to one end thereof; and
    a fluid management system for controllably inflating and deflating the balloon, the fluid management system including:
        a reservoir for storing balloon fill media, wherein the reservoir is partitioned into a first compartment and a second compartment configured to store the balloon fill media with a vent providing fluid communication between the first compartment and the second compartment,
        an inlet port that is in fluid communication with the first compartment and includes an inlet valve that selectively permits air to flow into the first compartment;
        an outlet port that is in fluid communication with the first compartment and includes an outlet valve that selectively permits air to exit from the first compartment;
        a fluid circuit for delivering the balloon fill media from the second compartment to the balloon and for returning the balloon fill media along a return line from the balloon to the second compartment;
        an applied vacuum that is in selective communication with the first compartment of the reservoir by virtue of an applied vacuum valve and is configured to generate negative pressure within the reservoir and creation of a pressure differential along the return line of the fluid circuit for controlling an internal pressure within the balloon; and
        a plurality of valves located along the fluid circuit to define a plurality of operating modes depending upon on/off states of the plurality of valves, wherein the plurality of operating modes includes: (1) a normal mode in which the fluid circuit is configured such that the balloon fill media can flow along the fluid circuit to the balloon and can flow along the return line to the reservoir and (2) a trapped volume mode in which the balloon fill media continuously flows along the fluid circuit in a manner in which the balloon fill media is not returned to the second compartment of the reservoir.

2. The balloon catheter system of claim 1, wherein the fluid circuit comprises a delivery line for delivering the balloon fill media from the second compartment to the balloon, wherein the plurality of valves comprises a first valve (V1) is provided along the delivery line, a third valve (V3) is provided along the return line, and a second valve (V2) is provided along a connecting conduit that extends between the delivery line and the return line for selectively defining a closed loop, when the system operates in the trapped volume mode, in which the balloon fill media flows from the return line to the delivery line via the connecting conduit when the first valve (V1) is closed and the second valve (V2) and the third valve (V3) are open.

3. The balloon catheter system of claim 1, wherein a first partition wall separates the first compartment from the second compartment and a second partition wall separates the first compartment from an upper space, the inlet port and the outlet port being contained in the upper space and the applied vacuum comprising a vacuum conduit that passes through the upper space and is in fluid communication with the first compartment.

4. The balloon catheter system of claim 3, wherein the applied vacuum includes a vacuum line pump that operates on the vacuum conduit.

5. The balloon catheter system of claim 3, wherein the fluid circuit comprises a delivery line for delivering the balloon fill media from the second compartment to the balloon, wherein the plurality of valves comprises a first valve (V1) is provided along the delivery line, a third valve (V3) is provided along the return line, and a second valve (V2) is provided along a connecting conduit that extends between the delivery line and the return line for selectively defining a closed loop; and wherein the connecting conduit is located within the upper space.

6. The balloon catheter system of claim 5, wherein the first valve, the second valve, and the third valve are located within the upper space.

7. The balloon catheter system of claim 5, wherein the second partition wall includes a first through hole in communication with the inlet port, a second through hole in communication with the outlet port and a third through hole in communication with the vacuum conduit.

8. The balloon catheter system of claim 3, wherein the applied vacuum valve comprises a check valve that opens under negative pressure to provide direct communication between the vacuum conduit and the first compartment.

9. The balloon catheter system of claim 8, wherein the internal pressure is between 0.2 psi and 1 psi.

10. The balloon catheter system of claim 1, wherein the fluid circuit comprises a delivery line for delivering the balloon fill media from the second compartment to the balloon, the delivery line including a first controllable pump.

* * * * *